(12) United States Patent
Haas et al.

US008703451B2

(10) Patent No.: US 8,703,451 B2
(45) Date of Patent: Apr. 22, 2014

(54) METHOD FOR THE PRODUCTION OF FREE CARBOXYLIC ACIDS

(75) Inventors: Thomas Haas, Muenster (DE); Thomas Tacke, Alzenau (DE); Achim Marx, Gelnhausen (DE); Alexander Schraven, Issum (DE); Olivier Zehnacker, Recklinghausen (DE); Eva Maria Wittmann, Traunreut (DE)

(73) Assignee: Evonik Roehm GmbH, Darmstadt (DE)

( * ) Notice: Subject to any disclaimer, the term of this patent is extended or adjusted under 35 U.S.C. 154(b) by 584 days.

(21) Appl. No.: 13/002,519

(22) PCT Filed: Apr. 29, 2009

(86) PCT No.: PCT/EP2009/055163
§ 371 (c)(1),
(2), (4) Date: Jan. 4, 2011

(87) PCT Pub. No.: WO2010/000506
PCT Pub. Date: Jan. 7, 2010

(65) Prior Publication Data
US 2011/0189742 A1    Aug. 4, 2011

(30) Foreign Application Priority Data
Jul. 4, 2008 (DE) .................. 10 2008 040 193

(51) Int. Cl.
*C12P 7/40* (2006.01)
*C07C 51/47* (2006.01)
*C07C 51/41* (2006.01)
*C12P 7/42* (2006.01)

(52) U.S. Cl.
CPC ... *C12P 7/40* (2013.01); *C12P 7/42* (2013.01); *C07C 51/47* (2013.01); *C07C 51/41* (2013.01)
USPC .................... 435/136; 562/513

(58) Field of Classification Search
CPC ............. C12P 7/40; C12P 7/42; C07C 51/47; C07C 51/41
USPC ......................... 453/136; 562/513
See application file for complete search history.

(56) References Cited

U.S. PATENT DOCUMENTS

| 4,405,717 | A |   | 9/1983  | Urbas          |         |
|-----------|---|---|---------|----------------|---------|
| 4,444,881 | A |   | 4/1984  | Urbas          |         |
| 5,817,870 | A |   | 10/1998 | Haas et al.    |         |
| 5,831,121 | A |   | 11/1998 | Haas et al.    |         |
| 6,066,763 | A | * | 5/2000  | Hayakawa ..... | 562/581 |
| 7,019,170 | B2| * | 3/2006  | Eyal et al. .. | 562/589 |
| 7,393,972 | B2|   | 7/2008  | Pascaly et al. |         |
| 2010/0021977 | A1 |   | 1/2010  | May et al.  |         |
| 2010/0035314 | A1 |   | 2/2010  | Mueller et al. |     |
| 2010/0068773 | A1 |   | 3/2010  | Marx et al. |         |
| 2010/0190224 | A1 |   | 7/2010  | Poetter et al. |     |
| 2010/0210871 | A1 |   | 8/2010  | Kobler et al. |      |
| 2010/0291644 | A1 |   | 11/2010 | Marx et al. |         |

FOREIGN PATENT DOCUMENTS

| EP | 0 359 043     | 3/1990 |
|----|---------------|--------|
| JP | 2007 082490   | 4/2007 |
| RU | 2 225 445 C2  | 3/2004 |
| WO | 00 14052      | 3/2000 |

OTHER PUBLICATIONS

U.S. Appl. No. 61/239,634, filed Sep. 3, 2009, Kobler, et al.
U.S. Appl. No. 13/141,456, filed Jun. 22, 2011, Schraven, et al.
International Search Report issued Dec. 30, 2009 in PCT/EP09/55163 filed Apr. 29, 2009.
Wasewar, Kailas L. et al. "Fermentation of Glucose to Lactic Acid Coupled with Reactive Extraction: A Review", Industrial & Engineering Chemistry Research, vol. 43, No. 19, pp. 5969-5982, XP002559880, (Sep. 15, 2004).
Chen, Rongfu et al., "Membrane-Mediated Extractive Fermentation for Lactic Acid Production from Cellulosic Biomass", Applied Biochemistry and Biotechnology, vol. 63-65, pp. 435-448, XP008087560, ISSN: 0273-2289, (Jan. 1, 1997).
Lewis, Vivian P. et al., "Novel Extractive Fermentation Process for Propionic Acid Production from Whey Lactose", Biotechnology Progress, vol. 8, No. 2, pp. 104-110, XP002559991, (Mar. 2, 1992).
Martak, Jan et al., "Toxicity of organic solvents used in situ in fermentation of lactic acid by Rhizopus arrhizus", Biotechnology Techniques, vol. 11, No. 2, pp. 71-75, XP019232506, ISSN:1573-6784, (Feb. 1, 1997).
Keshav, Amit et al., "Extraction of propionic acid with tri-n-octyl amine in different diluents", Separation and Purification Technology, vol. 63, No. 1, pp. 179-183, XP024528103, ISSN: 1383-5866, (Apr. 20, 2008).
Demirci, Ali et al., "Rapid screening of solvents and carrier compounds for lactic acid recovery by emulsion liquid extraction and toxicity on *Lactobacillus casei* (ATCC 11443)", Bioseparation, vol. 7, No. 6, pp. 297-308, XP019232354, ISSN: 1573-8272, (Nov. 1, 1998).
U.S. Appl. No. 13/054,002, filed Jan. 13, 2011, Haas, et al.
U.S. Appl. No. 13/001,204, filed Dec. 23, 2010, Reinecke, et al.
U.S. Appl. No. 12/950,752, filed Nov. 19, 2010, Mueller, et al.
U.S. Appl. No. 13/500,041, filed Apr. 3, 2012, Reinecke, et al.

\* cited by examiner

*Primary Examiner* — Yong Chu
(74) *Attorney, Agent, or Firm* — Oblon, Spivak, McClelland, Maier & Neustadt, L.L.P.

(57) ABSTRACT

A process for the preparation of free carboxylic acids including: A) preparation of carboxylic acid by a biological cell located in an aqueous medium with addition of an amine of formula (I)

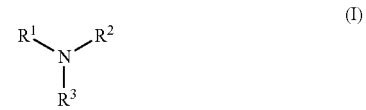

where $R^1$, $R^2$ and $R^3$, independently of one another, are identical or different, branched or unbranched, optionally substituted hydrocarbon radicals or H; B) for cases where the added amine A) is water-soluble, addition of a water-insoluble amine of formula (I), where, in A) or B), a multiphase system is obtained and the corresponding ammonium carboxylate is formed from the water-insoluble amine and the carboxylic acid; C) removal of the water-insoluble phase; and D) heating of the water-insoluble phase with release of free carboxylic acid.

20 Claims, 4 Drawing Sheets

METHOD FOR THE PRODUCTION OF FREE CARBOXYLIC ACIDS

CROSS-REFERENCE TO RELATED APPLICATIONS

The present application is a 35 U.S.C. §371 National Stage patent application of International patent application PCT/EP2009/055163, filed on Apr. 29, 2009, which claims priority to German patent application DE 102008040193.5, filed on Jul. 4, 2008.

FIELD OF THE INVENTION

The invention relates to a process for the preparation of free carboxylic acids comprising the process steps
A) preparation of carboxylic acid by a biological cell located in an aqueous medium with addition of an amine of the general formula (I)

formula (I)

where $R^1$, $R^2$ and $R^3$, independently of one another, are identical or different, branched or unbranched, optionally substituted hydrocarbon radicals or H,
B) for cases where the added amine in process step A) is water-soluble, addition of a water-insoluble amine of the general formula (I),
where, in process step A) and/or B), a multiphase system is obtained and the corresponding ammonium carboxylate is formed from the water-insoluble amine and the carboxylic acid, and
C) removal of the water-insoluble phase and
D) heating of the water-insoluble phase with release of free carboxylic acid.

PRIOR ART

The biochemical preparation of carboxylic acids is well known on account of, for example, the production of lactic acid or citric acid. Since most fermentation processes are carried out at a pH of the medium which is above the $pK_a$ value of the carboxylic acid to be prepared, the carboxylic acids are for the large part produced as salt and not as free acid. These carboxylates are mostly converted to their free acids by adding acids.

WO9815517 describes a process for the extraction of lactic acid using a basic, organic solvent and/or water-immiscible amines.

DE 102006052311 describes a process for the preparation of free α-hydroxycarboxylic acids by heating the corresponding ammonium carboxylates in the presence of tertiary amines with distillative removal of the ammonia which is formed, followed by further distillation and associated formation of the tertiary amine and of the free α-hydroxycarboxylic acid.

U.S. Pat. No. 4,275,234 describes an extractive process of carboxylic acids with amines as extractants comprising an additional, aqueous back-extraction step which leaves the carboxylic acid again present in aqueous solution.

U.S. Pat. No. 4,444,881 describes a process for the isolation of organic acids from fermentation broth by converting the acid into its calcium salt, admixing a water-soluble tertiary amine carbonate to form the trialkylammonium salt and precipitating calcium carbonate, concentrating the trialkylammonium salt solution and splitting the trialkylammonium salt through heating.

EP 1385593 describes a process for the work-up of short-chain carboxylic acids from a solution of their alkylammonium complexes by distillation with addition of an azeotroping hydrocarbon under conditions under which the alkylammonium complex decomposes into the free short-chain carboxylic acid and the alkylamine.

U.S. Pat. No. 5,510,526 describes a process for the work-up of free lactic acid from a fermentation broth by extraction with an extractant comprising a water-immiscible trialkylamine having a number of at least 18 carbon atoms in the presence of $CO_2$, separation of the organic phase from the aqueous phase and final separation of the free lactic acid from the organic phase.

WO02090312 describes a process for the purification of free carboxylic acids from aqueous solutions in which the aqueous solution is heated as a mixture with an organic solvent and, in so doing, the free acid is obtained.

U.S. Pat. No. 5,132,456 describes a multistage process for the purification of free carboxylic acids from an aqueous medium, in which firstly the carboxylic acid is extracted with an acid-absorbing agent and, following removal of this agent from the aqueous medium from/of this acid-absorbing agent with water-soluble amines, the carboxylic acid is back-extracted again as ammonium carboxylate. The ammonium carboxylate is then split.

A disadvantage of all of the processes is that large amounts of aqueous substance streams are formed or products arise which cannot be returned again to the process and are thus left over as waste.

It was an object of the invention to provide a process which overcomes the aforementioned disadvantages of the prior art.

DESCRIPTION OF THE INVENTION

Surprisingly, it has been found that a process for the preparation of free carboxylic acids comprising the process steps preparation of carboxylic acid through a biological cell with addition of an amine and optionally in cases where this added amine is water-soluble, addition of a further, water-insoluble amine, removal of the water-insoluble phase and heating of same with release of free carboxylic acid, achieves the object of the invention.

It is an advantage of the invention that acidification of the reaction solutions with, for example, mineral acids or carbon dioxide is dispensed with. As a result, the formation of large amounts of salt, such as, for example, ammonium sulphate or gypsum, as often arises in other processes, does not occur.

It is a further advantage that water is separated off early in the process in an energetically favourable manner, through, for example, phase separation, and thus further energy-consuming substance streams in the process are reduced. It is likewise not necessary to evaporate these substance streams.

A further advantage of the present invention is the fact that the product inhibition which often arises in biochemical processes can be avoided through use of a water-insoluble amine.

Within the context of the present invention, the term "carboxylic acid" includes both the free carboxylic acid (—COOH) and also the corresponding salt (—COO⁻).

Within the context of the present invention, the term "hydroxycarboxylic acid" describes carboxylic acids with at least one hydroxyl group and one carboxylic acid group and includes both the free carboxylic acid (—COOH) and also the corresponding salt (—COO⁻).

Within the context of the present invention, the term "ammonium carboxylate" includes all carboxylates of a monovalently positively charged group with a tetravalent nitrogen. The following general formula may be given as an example where $R^{1'}$, $R^{2'}$, $R^{3'}$ and $R^{4'}$, independently of one another, are identical or different, branched or unbranched, optionally substituted hydrocarbon radicals or H.

Within the context of the present invention, the term "water-insoluble" is defined as a solubility of less than 100 g/kg of aqueous solution.

Within the context of the present invention, the term "water-soluble" is defined as a solubility of equal to or more than 100 g/kg of aqueous solution.

Unless stated otherwise, all of the percentages given (%) are percentages by mass.

The invention therefore provides a process for the preparation of free carboxylic acids comprising the process steps
A) preparation of carboxylic acid by a biological cell located in an aqueous medium with addition of an amine of the general formula (I)

formula (I)

where $R^1$, $R^2$ and $R^3$, independently of one another, are identical or different, branched or unbranched, optionally substituted hydrocarbon radicals or H,
B) for cases where the added amine in process step A) is water-soluble, addition of a water-insoluble amine of the general formula (I),
where, in process step A) or rather B), a multiphase system is obtained and the corresponding ammonium carboxylate is formed from the water-insoluble amine and the carboxylic acid, and
C) removal of the water-insoluble phase and
D) heating of the water-insoluble phase with release of free carboxylic acid.

Within the context of the present invention, preferred carboxylic acids are selected from the group comprising acetic acid, propionic acid, butyric acid, isobutyric acid, malonic acid and succinic acid.

Within the context of the process according to the invention, it is likewise preferred that the carboxylic acid is a hydroxycarboxylic acid.

One group of preferred hydroxycarboxylic acids includes α-hydroxycarboxylic acids. These are preferably lactic acid, citric acid, tartaric acid, glycolic acid and 2-hydroxy-isobutyric acid, with 2-hydroxyisobutyric acid being particularly preferred.

A further group of preferred hydroxycarboxylic acids comprises β-hydroxycarboxylic acids. These are preferably 3-hydroxy-propionic acid, 3-hydroxybutyric acid, 3-hydroxyvaleric acid, 3-hydroxyhexanoic acid, 3-hydroxyheptanoic acid, 3-hydroxy-octanoic acid and 3-hydroxyisobutyric acid, with 3-hydroxy-isobutyric acid being particularly preferred.

In process step A, carboxylic acids are prepared through a biological cell located in an aqueous medium in accordance with the process known to the person skilled in the art. The process parameters are adapted accordingly depending on the cell used and the carboxylic acid prepared. These processes may, for example, be fermentative processes.

It is preferred that the cell used in process step A) is a microorganism.

The cell used is preferably selected from the group of the genera comprising:
*Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium* and *Cupriavidus*.

The cell used is particularly preferably selected from the group comprising *Aspergillus nidulans, Aspergillus niger, Alcaligenes latus, Bacillus megaterium, Bacillus subtilis, Brevibacterium flavum, Brevibacterium lactofermentum, Escherichia coli, Saccharomyces cerevisiae, Kluveromyces lactis, Candida blankii, Candida rugosa, Corynebacterium glutamicum, Corynebacterium efficiens, Zymomonas mobilis, Yarrowia lipolytica, Hansenula polymorpha, Methylobacterium extorquens, Ralstonia eutropha*, in particular *Ralstonia eutropha H16, Rhodospirillum rubrum, Rhodobacter sphaeroides, Paracoccus versutus, Pseudomonas aeruginosa, Pseudomonas putida, Acinetobacter calcoaceticus* and *Pichia pastoris*,
with *Escherichia coli, Yarrowia lipolytica, Corynebacterium glutamicum* and *Ralstonia eutropha* being very particularly preferred.

A particular embodiment of the process according to the invention is characterized in that, in process step A), a cell is used which is able to form carboxylic acids from at least one carbon source selected from the group consisting of carbon dioxide and carbon monoxide. This case thus involves using acetogenically and/or autotrophically growing cells, preferably those selected from the group comprising *Acetogenium kivui, Acetobacterium woodii, Acetoanaerobium noterae, Clostridium Aceticum, Butyribacterium methylotrophicum, Clostridium acetobutylicum, Clostridium thermoaceticum, Eubacterium limosum, Peptostreptococcus productus, Clostridium ljungdahlii, Ralstonia eutropha* and *Clostridium carboxydivorans*.

The amine added in process step A) may be ammonia and alkylamines; primary, secondary and tertiary alkylamines and also quaternary amine salts can be used here.

It is preferred that the added amine in process step A) is used in order to influence the pH of the aqueous medium, preferably to increase it.

Preferably, the pH is kept by the added amine in process step A) in a range from up to 2 to 9, preferably from 4 to 8, particularly preferably from 5 to 7.

Preferably, the amines used in process step A) are water-insoluble amines. In process step A), preference is given to using amines in which $R^1$, $R^2$ and $R^3$, independently of one another, are identical or different, unbranched, unsubstituted alkyl radicals having preferably 2 to 20, particularly preferably 4 to 16, very particularly preferably 6 to 12, carbon atoms, or H.

Preferably, in process step A), the water-insoluble amines are alkylamines having at least 16 carbon atoms, preferably trialkylamines and particularly preferably trialkylamines selected from the group comprising trihexylamines, trioctylamine, tridecylamine, tricaprylamines, tridodecylamines.

In particular embodiments of the process according to the invention, it may be advantageous to use amines with a relatively high basic strength in process step A); in this case, it is preferred that the amines used are dialkylamines and preferably dialkylamines selected from the group comprising diisotridecylamine, bis(2-ethylhexyl)amine, lauryl-trialkylmethylamines, diundecylamine, didecylamine.

In process step A), the amine is added at least in the molar ratio of 1.1:1, preferably from 1.5 to 5:1, based on the carboxylic acid.

After or else continuously during process step A), the liquid fractions or some of the liquid fractions and the biological cells can be separated from one another by methods known to the person skilled in the art, such as, for example, centrifugation, tangential filtration etc. If appropriate, separated-off components such as aqueous medium or cells can be returned to the process.

If appropriate, the liquid components obtained in process step A) can be concentrated before the further process steps.

As added amine in process step B), it is possible to use all water-insoluble amines known to the person skilled in the art, preferably alkylamines. Preference is given to using water-insoluble amines in process step B) in which $R^1$, $R^2$ and $R^3$, independently of one another, are identical or different, unbranched, unsubstituted alkyl radicals having preferably 2 to 20, particularly preferably 4 to 16, very particularly preferably 6 to 12 carbon atoms, or H.

Further preferably used amines correspond to the aforementioned water-insoluble amines in process step A).

The amine is added in process step B) at least in the molar ratio of 1.1:1, preferably from 1.5 to 5:1, based on the carboxylic acid.

In process step B), the water-soluble amine of process step A) can be at least partially removed.

Particularly if in process step B) a water-insoluble amine is used which is a weaker base (has a lower $pK_b$) than the water-soluble amine, it is preferred if at least some of the water-soluble amine is removed.

This can be achieved, for example, through an extraction, an ion exchanger, by heating and thus thermal expulsion of the water-soluble amine, or else by introducing $CO_2$, in which case the water-soluble amine precipitates out as carbonate. One exemplary process for separating off the water-soluble amine is described in DE 102006052311.

The removed water-soluble amine can be returned to process step A).

After process step A) and/or B), a multiphase system is present, and the corresponding ammonium carboxylate has formed from the water-insoluble amine and the carboxylic acid.

The ammonium carboxylate is preferably—based on identical volumes of aqueous to organic phases—for the large part, preferably to more than 60%, particularly preferably to more than 80% and very particularly preferably to more than 90%, present in a water-insoluble phase.

An additional, water-insoluble solvent can optionally be added to the water-insoluble amine in order to ensure advantageous properties such as, for example, better phase separations or more stable phases, to reduce the viscosity of the amine or to increase the solubility of the carboxylic acid.

Additional, water-insoluble solvents which can be used are, for example, alcohols with at least eight carbon atoms, ketones, such as, for example, methyl isobutyl ketone, aromatic solvents such as, for example, toluene and xylene, aliphatic nonpolar solvents, such as, for example, kerosin and hexane. Preference is given to using oleyl alcohol and dodecanol.

Preference is given to using those additional solvents whose boiling point is above the boiling point of the water-insoluble amine.

In process step C), water-insoluble phases comprising the ammonium carboxylate are separated off from the aqueous phase. This can be carried out by any methods known to the person skilled in the art with which organic phases can be separated from aqueous phases, such as, for example, decantation, centrifugation or else distillation. Examples thereof can be found, inter alia, in Perry's Chemical Engineers' Handbook (Section 15); by Robert H Perry, Don W Green, James 0 Malone; published 1999; McGraw-Hill.

Within the context of the process according to the invention, it may be advantageous for the separated-off aqueous water phase to be returned to the process.

It may likewise be advantageous to further purify the separated-off water-insoluble phase, such as, for example, through extraction, filtration, centrifugation, ion exchangers or concentration, such as, for example, through distillation, extraction.

The release of free carboxylic acid in process step D) takes place by heating the water-insoluble phase, preferably under reduced pressure, as a result of the splitting of the ammonium carboxylate.

Within the context of the invention, a reduced pressure means a pressure of less than $1*10^5$ Pa, preferably less than $0.9*10^5$ Pa and particularly preferably less than $0.8*10^5$ Pa.

The type of heating is dependent on the apparatus/plant used and can take place, for example, via a heating bath, a heatable reactor jacket or by contacting the water-insoluble phase with a heated gas stream. The temperature is selected, depending on the related pressure, such that the thermal salt splitting takes place and the formation of by-products is minimized. Preferably, at the same time at least some of the carboxylic acid formed during the reaction is removed by distillation. Suitable temperature and pressure ranges can be determined by a person skilled in the art, as can the required duration of the thermal treatment, for example by monitoring the amount of amine and/or carboxylic acid formed or the temperature course of the reaction solution.

In a preferred embodiment, the temperature in process step D) is in a temperature range from 80° C. to 300° C., preferably from 120° C. to 250° C., particularly preferably from 150° C. to 220° C.

The water-insoluble amine obtained in process step D) can be returned to the process.

The product fraction obtained in process step D) comprising carboxylic acids can be reacted to give secondary products without further purification. Within the context of the invention, preference is given, for example, to the dehydration of hydroxycarboxylic acids to unsaturated carboxylic acids.

A series of processes for the dehydration of hydroxycarboxylic acids are known to the person skilled in the art, such processes being described, for example, in PCT/EP2007/055394, U.S. Pat. Nos. 3,666,805 and 5,225,594.

The process according to the invention can furthermore comprise one or more subsequent steps for the purification and isolation of the carboxylic acids from the product fraction. Suitable process steps are, inter alia, concentration, crystallization, ion exchange chromatography, electrodialysis, extraction with reactive solvents and purification through esterification of the carboxylic acid with suitable alcohols, subsequent distillation of the resulting ester and subsequent hydrolysis of the ester to give the free acid, and combinations of these steps. By-products present in the product fraction can be removed before or after isolating the free carboxylic acid formed during the thermal salt splitting, or reacted to give the carboxylic acid.

In the examples given below, the present invention is described by way of example without any intention to limit the invention, the scope of application of which arises from the entire description and the claims, to the embodiments given in the examples.

The following figures form part of the examples.

EXAMPLES

Biocompatibility of TOA (trioctylamine) with Ralstonia eutropha Cultures of *Ralstonia eutropha* PHB-4 (reclassified as *Cupriavidus necator*, DSMZ 541) transformed with the plasmid: pBBR1MCS-2::icmA-icmB with SEQ ID No. 1 were fermented on a 400 ml scale in a standard medium for 46 hours to an OD (optical density at 600 nm) of ca. 30, which corresponds to a CFU (colony formed units) of $1 \times 10^{11}$ per ml, under standard conditions (30° C.; pH 6.8; rpm 250-750; $pO_2$ 20%).

After a fermentation time of 48 hours, 0.5%, 1%, 5% and 10% (w/v) trioctylamine (TOA) were added under sterile conditions. After a further 6 and 20 hours the CFU were determined.

To ascertain the CFU, dilution series of the broths were prepared. The dilutions were plated out onto agar plates and incubated for 24 hours at 30° C. A four-fold determination of the dilutions $10^7$ and $10^8$ was carried out.

Result: The CFU increased further over a period of 20 hours (fermentation time 46-65 hours) in the presence of TOA (0.5%, 1%, 5% and 10% (w/v)).

The values are summarized in the table below, the CFU values are standardized to 1 ml of fermentation broth.

|  | 0 h | 6 h | 24 h |
| --- | --- | --- | --- |
| 0.5% TOA | 3.75U + 10 | 5.31U + 10 | 6.00U + 10 |
| 1% TOA | 3.60U + 10 | 3.73U + 10 | 1.44U + 11 |
| 5% TOA | 1.44U + 11 | 1.25U + 11 | 8.08U + 11 |
| 10% TOA | 1.34U + 11 | 1.61U + 11 | 1.82U + 11 |

Preparation of Carboxylic Acid Through a Biological Cell Located in an Aqueous Medium in the Presence of a Trialkylamine 2-Hydroxyisobutyric-acid-producing *Ralstonia eutropha* PHB-4 (reclassified as *Cupriavidus necator*, DSMZ 541), which have been transformed with the plasmid pBBR1MCS-2::icmA-icmB, SEQ ID No. 1, were grown as two 50 ml cultures in a shaking incubator under standard conditions (30° C., 140 rpm, 20 h) in LB medium.

From this, for the biomass production, 5×10 ml were inoculated over into 40 ml of modified mineral salt medium (in accordance with Schlegel et al., 1961) and incubated for 10 h under standard conditions The biomass cultures were centrifuged off and resuspended in 10 ml of modified mineral salt medium.

Using the resuspensions, 5 flasks of a Ramos shaking incubator (Respiration Activity Monitoring System) were inoculated. The flasks were filled with modified mineral salt medium (addition of 1 g/l of yeast extract and 15 g/l of fructose) with vitamin B12 (60 mg/l). 3 flasks additionally comprised 1, 5 and 10% (w/v) of trioctylamine (TOA).

The flasks were incubated for 24 h under standard conditions (30° C., 140 rpm).

After 0, 15 and 24 hours, samples were taken and CFU (OD), pH, and 2HIB concentration in the broth were determined.

For the CFU determination, dilution series of the broths were prepared. The dilutions were plated out onto LB agar plates with 300 mg/l of Kanamycin and incubated for 24 h at 30° C. A 4-fold determination of the dilutions $10^{-8}$ and $10^{-9}$ was carried out.

Figure 1:
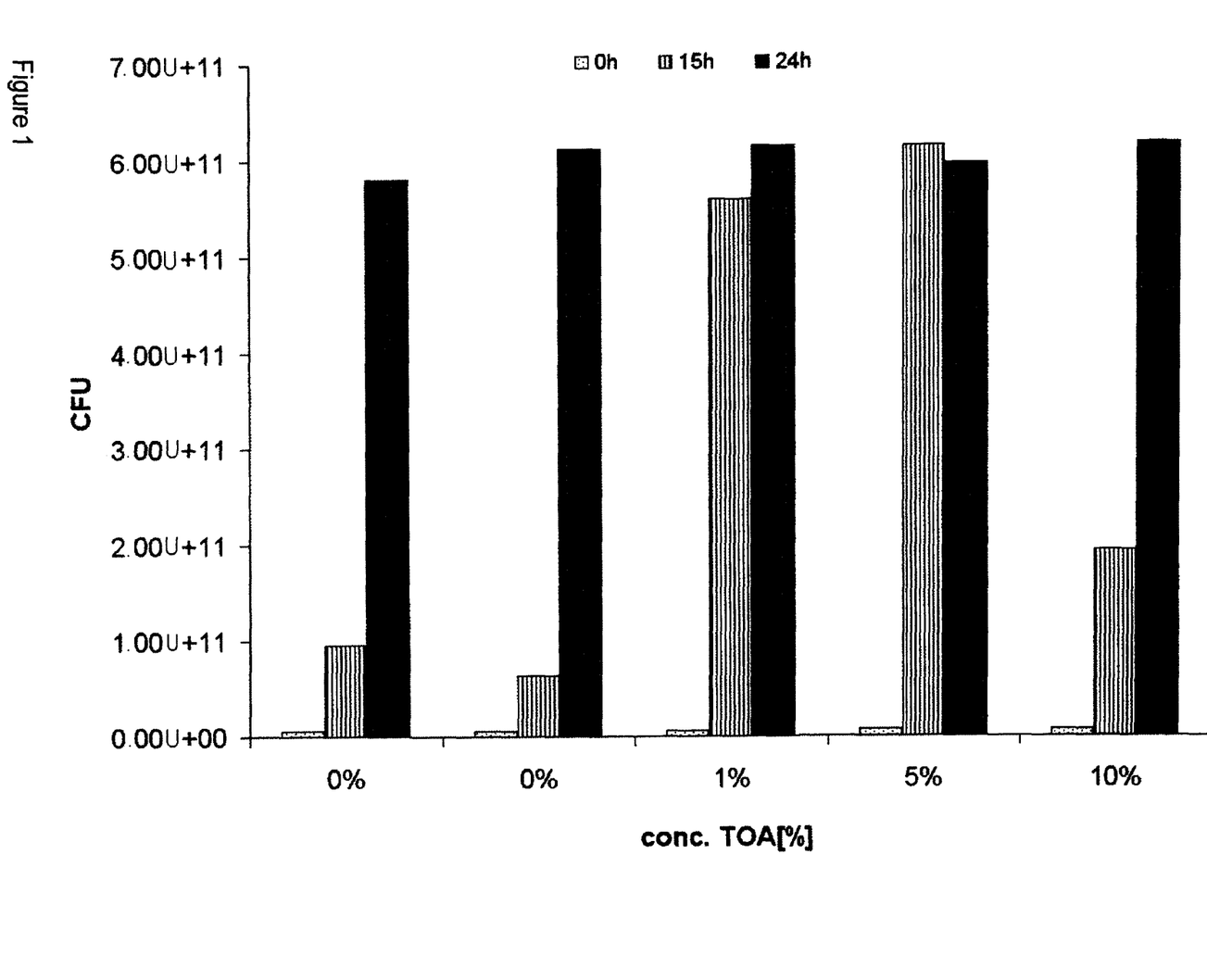
FIG. 1: Growth of cells in the presence of various TOA concentrations

FIG. 1 shows the results of the cultivations, CFU values are standardized to 1 ml of fermentation broth. The cell growth is evidently not influenced by the presence of the alkylamine.

The determination of the concentration of the prepared carboxylic acid 2-hydroxyisobutyric acid was carried out by means of ion chromatography (IC) (Methrom 761 Compact with Autosampler, Method Dionex AS154×250 mm+precolumn AG 154×350 ml) and HPLC (Agilent Technologies HPLC series 1200, Method Aminex).

Figure 2:
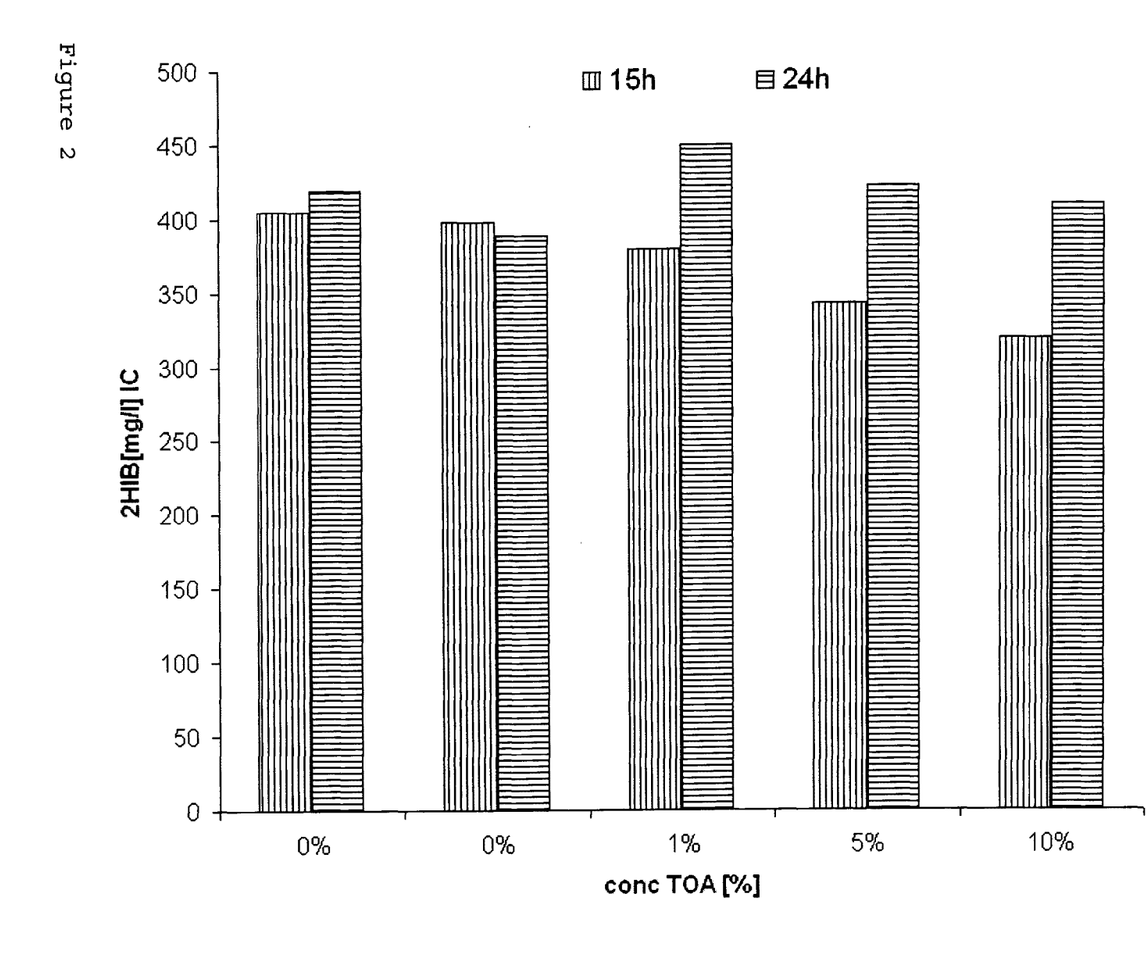
FIG. 2: Preparation of 2-hydroxyisobutyric acid in the presence of various TOA concentrations

FIG. 2 shows the IC measurement value of the aforementioned cultivations of the 2-HIB concentrations.

In all batches, 2-hydroxyisobutyric acid is formed throughout the entire experimental period.

Thermal Splitting of an Alkyl Ammonium Salt

A trioctylammonium salt solution was prepared by mixing 2-hydroxyisobutyric acid (2-HIB) with trioctylamine (TOA). For this, 10 g of 2-hydroxyisobutyric acid were weighed in and dissolved in 90 g of TOA. This initial weight results in a stoichiometric ratio of TOA/2-hydroxyisobutyric acid of 2.64. 50.6 g of this trioctylammonium salt solution were initially introduced in a rotary evaporator. For the thermal salt splitting, an absolute pressure of 27 mbar was established by means of a vacuum pump. The oil bath used for the thermal treatment of the initial charge was adjusted to 180° C. and kept constant. After about 20 min, white crystals crystallized out on the cool glass sections. After ca. 4 h, the experiment was terminated. Final weighing of the initial charge following thermal splitting revealed a mass reduction of 3.5 g. The white crystals located on the glass were washed with water and analysed by means of HPLC. This analysis showed that these crystals are 2-hydroxyisobutyric acid. Using elemental analysis (C, H, N, O), the samples were analysed both before the start of the experiment, and also after the end of the experiment. On the basis of these analyses, it was possible to calculate the concentrations and the quantitative amounts of the respective substances. 98.4% of the yielded TOA amount was still found in the initial charge after the experiment; 34.4% of the initial quantitative mass of the 2-hydroxyisobutyric acid were found at the end of the experiment also as trialkylammonium salt in the initial charge. 65.6% of the weighed-in 2-hydroxyisobutyric acid mass could be thermally split from the salt and partly be returned as crystals to the cool glass sections.

Exemplary Process Sketch with Use of a Water-Insoluble Amine in Process Step A)

Figure 3:
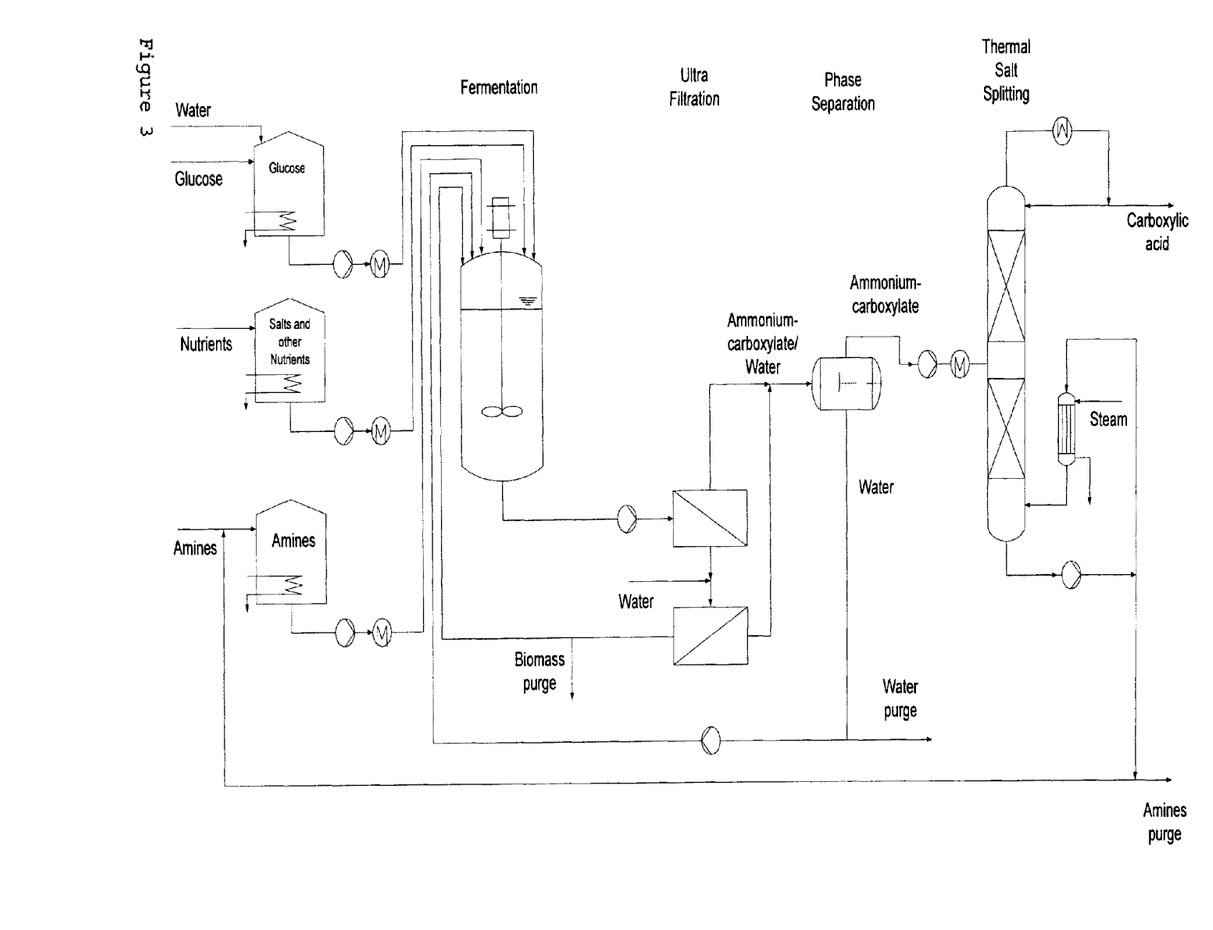
FIG. 3: Process sketch with use of a water-insoluble amine in process step A)

FIG. 3 describes a configuration of the process according to the invention in which, in process step A), a water-insoluble amine is used. These are used in the fermenter for regulating the pH. As a result, ammonium carboxylates are formed in the fermenter. After separating off the biomass, the water-insoluble phase and the aqueous phase can be separated. The aqueous phase can be returned to the fermenter, following purification if desired. The ammonium carboxylates are located in the water-insoluble phase. These can be split in a downstream thermal salt splitting into the free acid and the corresponding amine. Following purification if desired, the amine can again be returned to the fermenter for pH regulation and thus be circulated.

Exemplary Process Sketch with Use of a Water-soluble Amine in Process Step A)

Figure 4:
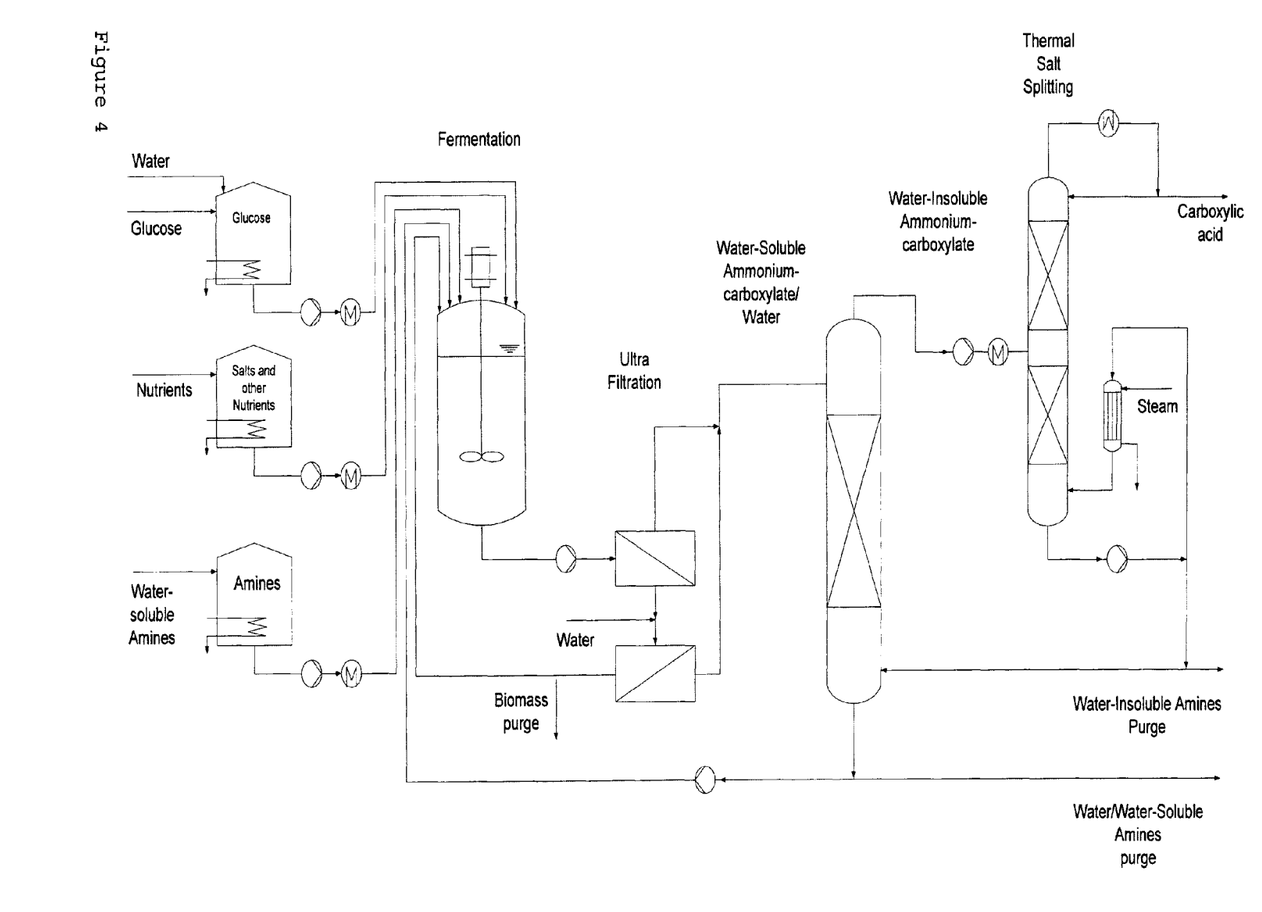
FIG. 4: Process sketch with use of a water-soluble amine in process step A)

FIG. 4 describes a configuration of the process according to the invention in which, in process step A), a water-soluble amine is used for regulating the pH. As a result of this, ammonium carboxylates are formed in the fermenter. After separating off the biomass, water-insoluble amines are added to the aqueous solution. In this process step B), the carboxylates are transferred to the organic phase and, if appropriate, the water-insoluble amines are partially removed. The organic phase is fed to the thermal salt splitting, whereby firstly the free acid and secondly the amines are formed. Both substance streams can, if required, be purified in a separate purification stage (not taken into consideration in the process). The amines obtained in this way can be returned to the process.

The invention claimed is:

1. A process for producing a free carboxylic acid, the process comprising:

A) synthesizing a carboxylic acid in an aqueous culture of cells, wherein the cells are cultured in the presence of a water-insoluble amine of formula (I)

(I)

wherein $R^1$, $R^2$ and $R^3$, independently of one another, are identical or different, branched or unbranched, optionally substituted hydrocarbon radicals or H,
to form a corresponding ammonium carboxylate from the water-insoluble amine and the synthesized carboxylic acid, wherein the ammonium carboxylate is present in a water-insoluble phase within the aqueous culture of cells;

B) removing the water-insoluble phase from the aqueous culture of cells; and

C) heating the removed water-insoluble phase, and thereby releasing the free carboxylic acid.

2. The process of claim 1, wherein the carboxylic acid is an α- or β-hydroxycarboxylic acid.

3. The process of claim 1, wherein $R^1$, $R^2$ and $R^3$, independently of one another, are identical or different, unbranched, unsubstituted alkyl radicals or H.

4. The process of claim 1, wherein, in C), the free carboxylic acid is released under reduced pressure.

5. The process of claim 1, wherein, in C), the free carboxylic acid is released in a temperature range from 80° C. to 300° C.

6. The process of claim 1, wherein the amine of formula (I) influences the pH of the aqueous culture of cells.

7. The process of claim 1, wherein, in C), the amine of formula (I) is recovered and returned to the process.

8. The process of claim 1, wherein the culture of cells in A) is a culture of microorganism cells.

9. The process of claim 1, wherein the cells in A) are selected from the group of genera consisting of:

Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium, and Cupriavidus.

10. The process of claim 1, wherein, in C), the free carboxylic acid is released in a temperature range from 120° C. to 250° C.

11. The process of claim 1, wherein, in C), the free carboxylic acid is released in a temperature range from 150° C. to 220° C.

12. The process of claim 1, wherein the cells are cultured in the presence of a water-soluble amine of formula (I) in addition to the water-insoluble amine of formula (I).

13. The process of claim 1, wherein the carboxylic acid is at least one selected from the group consisting of acetic acid, propionic acid, butyric acid, isobutyric acid, malonic acid and succinic acid.

14. The process of claim 1, wherein the carboxylic acid is at least one selected from the group consisting of lactic acid, citric acid, tartaric acid, glycolic acid, 2-hydroxyisobutyric acid, 3-hydroxypropionic acid, 3-hydroxybutyric acid, 3-hydroxyvaleric acid, 3-hydroxyhexanoic acid, 3-hydroxyheptanoic acid, 3-hydroxyoctanoic acid and 3-hydroxyisobutyric acid.

15. The process of claim 1, wherein, in A), the carboxylic acid is synthesized in the culture of cells from at least one carbon source selected from the group consisting of carbon dioxide and carbon monoxide.

16. The process of claim 1, wherein the pH in the culture of cells is from 2 to 9.

17. The process of claim 1, wherein the pH in the culture of cells is from 5 to 7.

18. The process of claim 1, wherein the water-insoluble amine is present in the aqueous culture of cells in a molar ratio of at least 1.1:1 relative to the carboxylic acid.

19. The process of claim 1, wherein the water-insoluble amine is present in the aqueous culture of cells in a molar ratio in a range of 1.5:1 to 5:1 relative to the carboxylic acid.

20. The process of claim 1, wherein $R^1$, $R^2$ and $R^3$, independently of one another, are identical or different, unbranched, unsubstituted alkyl radicals each having from 2 to 20 carbon atoms.

\* \* \* \* \*

SEQUENCE LISTING

<160> NUMBER OF SEQ ID NOS: 1

<210> SEQ ID NO 1
<211> LENGTH: 7296
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
accttcggga gcgcctgaag cccgttctgg acgccctggg gccgttgaat cgggatatgc        60
aggccaaggc cgccgcgatc atcaaggccg tgggcgaaaa gctgctgacg gaacagcggg       120
aagtccagcg ccagaaacag gcccagcgcc agcaggaacg cgggcgcgca catttccccg       180
aaaagtgcca cctgggatga atgtcagcta ctgggctatc tggacaaggg aaaacgcaag       240
cgcaaagaga aagcaggtag cttgcagtgg gcttacatgg cgatagctag actgggcggt       300
tttatggaca gcaagcgaac cggaattgcc agctggggcg ccctctggta aggttgggaa       360
gccctgcaaa gtaaactgga tggctttctt gccgccaagg atctgatggc gcagggatc        420 aagatctgat caagagacag gatgaggatc gtttcgcatg attgaacaag atggattgca       480
cgcaggttct ccggccgctt gggtggagag gctattcggc tatgactggg cacaacagac       540
aatcggctgc tctgatgccg ccgtgttccg gctgtcagcg caggggcgcc cggttctttt       600
tgtcaagacc gacctgtccg gtgccctgaa tgaactgcag gacgaggcag cgcggctatc       660
gtggctggcc acgacgggcg ttccttgcgc agctgtgctc gacgttgtca ctgaagcggg       720
aagggactgg ctgctattgg gcgaagtgcc ggggcaggat ctcctgtcat ctcaccttgc       780
tcctgccgag aaagtatcca tcatggctga tgcaatgcgg cggctgcata cgcttgatcc       840
ggctacctgc ccattcgacc accaagcgaa acatcgcatc gagcgagcac gtactcggat       900
ggaagccggt cttgtcgatc aggatgatct ggacgaagag catcagggc tcgcgccagc       960 cgaactgttc gccaggctca aggcgcgcat gcccgacggc gaggatctcg tcgtgaccca      1020
tggcgatgcc tgcttgccga atatcatggt ggaaaatggc cgcttttctg gattcatcga      1080
ctgtggccgg ctgggtgtgg cggaccgcta tcaggacata gcgttggcta cccgtgatat      1140
tgctgaagag cttggcggcg aatgggctga ccgcttcctc gtgctttacg gtatcgccgc      1200
tcccgattcg cagcgcatcg ccttctatcg ccttcttgac gagttcttct gagcgggact      1260
ctggggttcg aaatgaccga ccaagcgacg cccaacctgc catcacgaga tttcgattcc      1320
accgccgcct tctatgaaag gttgggcttc ggaatcgttt tccgggacgc cggctggatg      1380
atcctccagc gcggggatct catgctggag ttcttcgccc acccccatgg caaatatta      1440
```

```
tacgcaaggc gacaaggtgc tgatgccgct ggcgattcag gttcatcatg ccgtttgtga   1500
tggcttccat gtcggcagaa tgcttaatga attacaacag tttttatgca tgcgcccaat   1560
acgcaaaccg cctctccccg cgcgttggcc gattcattaa tgcagctggc acgacaggtt   1620
tcccgactgg aaagcgggca gtgagcgcaa cgcaattaat gtgagttagc tcactcatta   1680
ggcaccccag gctttacact ttatgcttcc ggctcgtatg ttgtgtggaa ttgtgagcgg   1740
ataacaattt cacacaggaa acagctatga ccatgattac gccaagcgcg caattaaccc   1800
tcactaaagg gaacaaaagc tgggtaccgg gccccccctc gaggtcgacg gtatcgataa   1860
gcttgatatc gaattcctgc agcccggggg atccactagt tctagaaata attttgttta   1920
actttaagaa ggaattcagg agcccttcac catgacctgg cttgagccgc agataaagtc   1980
ccaactccaa tcggagcgca aggactggga agcgaacgaa gtcggcgcct tcttgaagaa   2040
ggcccccgag cgcaaggagc agttccacac gatcgggac ttcccggtcc agcgcaccta   2100
caccgctgcc gacatcgccg acacgccgct ggaggacatc ggtcttccgg ggcgctaccc   2160
gttcacgcgc gggccctacc cgacgatgta ccgcagccgc acctggacga tgcgccagat   2220
cgccggcttc ggcaccggcg aggacaccaa caagcgcttc aagtatctga tcgcgcaggg   2280
ccagaccggc atctccaccg acttcgacat gcccacgctg atgggctacg actccgacca   2340
cccgatgagc gacggcgagg tcggccgcga gggcgtggcg atcgacacgc tggccgacat   2400
ggaggcgctg ctggccgaca tcgacctcga aagatctcg gtctcgttca cgatcaaccc   2460
gagcgcctgg atcctgctcg cgatgtacgt ggcgctcggc gagaagcgcg gctacgacct   2520
gaacaagctg tcgggcacgg tgcaggccga catcctgaag gagtacatgg cgcagaagga   2580
gtacatctac ccgatcgcgc cgtcggtgcg catcgtgcgc gacatcatca cctacagcgc   2640
gaagaacctg aagcgctaca acccgatcaa catctcgggc taccacatca gcgaggccgg   2700
ctcctcgccg ctccaggagg cggccttcac gctggccaac ctgatcacct acgtgaacga   2760
ggtgacgaag accggtatgc acgtcgacga attgcgccg cggttggcct tcttcttcgt   2820
gtcgcaaggt gacttcttcg aggaggtcgc gaagttccgc gccctgcgcc gctgctacgc   2880
gaagatcatg aaggagcgct tcggtgcaag aaatccggaa tcgatgcggt tgcgcttcca   2940
ctgtcagacc gcggcggcga cgctgaccaa gccgcagtac atggtcaacg tcgtgcgtac   3000
gtcgctgcag gcgctgtcgg ccgtgctcgg cggcgcgcag tcgctgcaca ccaacggcta   3060
cgacgaagcc ttcgcgatcc cgaccgagga tgcgatgaag atggcgctgc gcacgcagca   3120
gatcattgcc gaggagagtg gtgtcgccga cgtgatcgac ccgctgggtg gcagctacta   3180
cgtcgaggcg ctgaccaccg agtacgagaa gaagatcttc gagatcctcg aggaagtcga   3240
gaagcgcggt ggcaccatca agctgatcga gcagggctgg ttccagaagc agattgcgga   3300
cttcgcttac gagaccgcgc tgcgcaagca gtccggccag aagccggtga tcggggtgaa   3360
ccgcttcgtc gagaacgaag aggacgtcaa gatcgagatc cacccgtacg acaacacgac   3420
ggccgaacgc cagatttccc gcacgcgccg cgttcgcgcc gagcgcgacg aggccaaggt   3480
gcaagcgatg ctcgaccaac tggtggctgt cgccaaggac gagtcccaga acctgatgcc   3540
gctgaccatc gaactggtga aggccggcgc aacgatgggg gacatcgtcg agaagctgaa   3600
ggggatctgg ggtacctacc gcgagacgcc ggtcttctga gcaggaagct tcccaccatg   3660
gaccaaatcc cgatccgcgt tcttctcgcc aaagtcggcc tcgacggcca tgaccgaggc   3720
gtcaaggtcg tcgctcgcgc gctgcgcgac gccggcatgg acgtcatcta ctccggcctt   3780
catcgcacgc ccgaagaggt ggtcaacacc gccatccagg aagacgtgga cgtgctgggt   3840
```

```
gtaagcctcc tgtccggcgt gcagctcacg gtcttcccca agatcttcaa gctcctggac   3900
gagagaggcg ctggcgactt gatcgtgatc gccggtggcg tgatgccgga cgaggacgcc   3960
gcggccatcc gcaagctcgg cgtgcgcgag gtgctactgc aggacacgcc cccgcaggcc   4020
atcatcgact cgatccgctc cttggtcgcc gcgcgcggcg cccgctgaaa gggcgagctc   4080
tccaattcgc cctatagtga gtcgtattac gcgcgctcac tggccgtcgt tttacaacgt   4140
cgtgactggg aaaaccctgg cgttacccaa cttaatcgcc ttgcagcaca tccccctttc   4200
gccagctggc gtaatagcga agaggcccgc accgatcgcc cttcccaaca gttgcgcagc   4260
ctgaatggcg aatggaaatt gtaagcgtta atattttgtt aaaattcgcg ttaaattttt   4320
gttaaatcag ctcatttttt aaccaatagg ccgactgcga tgagtggcag ggcggggcgt   4380 aatttttta aggcagttat tggtgccctt aaacgcctgg tgctacgcct gaataagtga   4440
taataagcgg atgaatggca gaaattcgaa agcaaattcg acccggtcgt cggttcaggg   4500
cagggtcgtt aaatagccgc ttatgtctat tgctggttta ccggtttatt gactaccgga   4560
agcagtgtga ccgtgtgctt ctcaaatgcc tgaggccagt ttgctcaggc tctccccgtg   4620
gaggtaataa ttgacgatat gatcatttat tctgcctccc agagcctgat aaaaacggtg   4680
aatccgttag cgaggtgccg ccggcttcca ttcaggtcga ggtggcccgg ctccatgcac   4740
cgcgacgcaa cgcggggagg cagacaaggt atagggcggc gaggcggcta cagccgatag   4800
tctggaacag cgcacttacg ggttgctgcg caacccaagt gctaccggcg cggcagcgtg   4860
acccgtgtcg gcggctccaa cggctcgcca tcgtccagaa acacggctc atcgggcatc   4920 ggcaggcgct gctgcccgcg ccgttcccat tcctccgttt cggtcaaggc tggcaggtct   4980
ggttccatgc ccggaatgcc gggctggctg gcggctcct cgccggggcc ggtcggtagt   5040
tgctgctcgc ccggatacag ggtcgggatg cggcgcaggt cgccatgccc caacagcgat   5100
tcgtcctggt cgtcgtgatc aaccaccacg gcggcactga acaccgacag gcgcaactgg   5160
tcgcggggct ggccccacgc cacgcggtca ttgaccacgt aggccgacac ggtgccgggg   5220
ccgttgagct tcacgacgga gatccagcgc tcggccacca agtccttgac tgcgtattgg   5280
accgtccgca aagaacgtcc gatgagcttg gaaagtgtct tctggctgac caccacggcg   5340
ttctggtggc ccatctgcgc cacgaggtga tgcagcagca ttccgccgt gggtttcctc   5400 gcaataagcc cggcccacgc ctcatgcgct ttgcgttccg tttgcaccca gtgaccgggc   5460
ttgttcttgg cttgaatgcc gatttctctg gactgcgtgg ccatgcttat ctccatgcgg   5520
tagggtgccg cacggttgcg gcaccatgcg caatcagctg caacttttcg gcagcgcgac   5580
aacaattatg cgttgcgtaa aagtggcagt caattacaga ttttctttaa cctacgcaat   5640
gagctattgc gggggtgcc gcaatgagct gttgcgtacc cccctttttt aagttgttga   5700 ttttttaagtc tttcgcattt cgccctatat ctagttcttt ggtgcccaaa gaagggcacc   5760 cctgcgggt tccccacgc cttggcgcg gctcccctc cggcaaaaag tggcccctcc   5820
ggggcttgtt gatcgactgc gcggccttcg gccttgccca aggtggcgct gccccttgg   5880 aaccccgca ctcgccgccg tgaggctcgg ggggcaggcg ggcgggcttc gccttcgact   5940
gcccccactc gcataggctt gggtcgttcc aggcgcgtca aggccaagcc gctgcgcggt   6000
cgctgcgcga gccttgaccc gccttccact tggtgtccaa ccggcaagcg aagcgcgcag   6060
gccgcaggcc ggaggctttt ccccagagaa aattaaaaaa attgatgggg caaggccgca   6120
ggccgcgcag ttggagccgg tgggtatgtg gtcgaaggct gggtagccgg tgggcaatcc   6180
ctgtggtcaa gctcgtgggc aggcgcagcc tgtccatcag cttgtccagc agggttgtcc   6240
```

```
-continued
acgggccgag cgaagcgagc cagccggtgg ccgctcgcgg ccatcgtcca catatccacg    6300
ggctggcaag ggagcgcagc gaccgcgcag ggcgaagccc ggagagcaag cccgtagggc    6360
gccgcagccg ccgtaggcgg tcacgactt gcgaagcaaa gtctagtgag tatactcaag    6420
cattgagtgg cccgccggag gcaccgcctt gcgctgcccc cgtcgagccg gttggacacc    6480
aaaagggagg ggcaggcatg gcggcatacg cgatcatgcg atgcaagaag ctggcgaaaa    6540
tgggcaacgt ggcggccagt ctcaagcacg cctaccgcga gcgcgagacg cccaacgctg    6600
acgccagcag gacgccagag aacgagcact gggcggccag cagcaccgat gaagcgatgg    6660
gccgactgcg cgagttgctg ccagagaagc ggcgcaagga cgctgtgttg gcggtcgagt    6720
acgtcatgac ggccagcccg gaatggtgga agtcggccag ccaagaacag caggcggcgt    6780
tcttcgagaa ggcgcacaag tggctggcgg acaagtacgg ggcggatcgc atcgtgacgg    6840
ccagcatcca ccgtgacgaa accagcccgc acatgaccgc gttcgtggtg ccgctgacgc    6900
aggacggcag gctgtcggcc aaggagttca tcggcaacaa agcgcagatg acccgcgacc    6960
agaccacgtt tgcggccgct gtggccgatc tagggctgca acggggcatc gagggcagca    7020
aggcacgtca cacgcgcatt caggcgttct acgaggccct ggagcggcca ccagtgggcc    7080
acgtcaccat cagcccgcaa gcggtcgagc cacgcgccta tgcaccgcag ggattggccg    7140
aaaagctggg aatctcaaag cgcgttgaga cgccggaagc cgtggccgac cggctgacaa    7200
aagcggttcg gcaggggtat gagcctgccc tacaggccgc cgcaggagcg cgtgagatgc    7260
gcaagaaggc cgatcaagcc caagagacgg cccgag                              7296
```